United States Patent
Shafikhani

(10) Patent No.: US 9,606,107 B2
(45) Date of Patent: Mar. 28, 2017

(54) CRK—A NOVEL TARGET FOR CANCER THERAPY

(71) Applicant: Rush University Medical Center, Chicago, IL (US)

(72) Inventor: Sasha Shafikhani, Elmwood Park, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 15/062,941

(22) Filed: Mar. 7, 2016

(65) Prior Publication Data

US 2016/0258932 A1 Sep. 8, 2016

Related U.S. Application Data

(62) Division of application No. 14/008,032, filed as application No. PCT/US2012/031470 on Mar. 30, 2012, now abandoned.

(60) Provisional application No. 61/469,861, filed on Mar. 31, 2011.

(51) Int. Cl.
| | | |
|---|---|---|
| *C12Q 1/68* | (2006.01) | |
| *G01N 33/50* | (2006.01) | |
| *A61K 38/18* | (2006.01) | |
| *A61K 38/21* | (2006.01) | |
| *C12N 5/02* | (2006.01) | |

(52) U.S. Cl.
CPC .......... *G01N 33/5011* (2013.01); *A61K 38/18* (2013.01); *A61K 38/21* (2013.01); *G01N 33/502* (2013.01)

(58) Field of Classification Search
None
See application file for complete search history.

(56) References Cited

PUBLICATIONS

Fan et al., "Apoptosis-Induced Compensatory Proliferation. The Cell is Dead. Long Live the Cell!" Trends Cell Biology, 18(10): 467-473 (2008).
Shafikhani et al., "The Pseudomonas Aeruginosa Type III Secreted Toxin ExoT is Necessary and Sufficient to Induce Apoptosis in Epithelial Cells," Cellular Microbiology, 10(4): 994-1007 (2008).
Sriram et al., "Emerging Roles for Crk in Human Cancer," Genes and Cancer, 1(11): 1132-1139 (2011).
Rodrigues et al., "CrkI and CrkII Function as Key Signaling Integrators for Migration and Invasion of Cancer Cells", Mol. Cancer Research, 3(4): 183-194 (2005).
International Search Report dated Sep. 20, 2012 from Corresponding PCT Application No. PCT/US2012/031470.
Balachandran et al., "The ubiquitin ligase Cbl-b limits Pseudomonas aeruginosa exotoxin T-mediated virulence", Journal of Clinical Investigation, 117(2): 419-427 (2007).
Lecoeur, "Nuclear Apoptosis Detection by FlowCytometry: Influence of Endogenous Endonucleases", Experimental Cell Research, 277: 1-14 (2002).
Gupta et al., "Dominant-negative mutants of the SH2/SH3 adapters Nck and Grb2 inhibit MAP kinase activation and mesoderm-specific gene induction by eFGF in Xenopus", Oncogene, 17: 2155-2165 (1998).
Tanaka et al., "Differential Inhibition of Signaling Pathways by Dominant-Negative SH2/SH3 Adapter Proteins", Molecular and Cellular Biology, 15(12): 6829-6837 (1995).

*Primary Examiner* — Nancy J Leith
(74) *Attorney, Agent, or Firm* — McDermott Will & Emery LLP

(57) ABSTRACT

The invention features a method of identifying a therapeutically active compound that inhibits apoptotic compensatory signaling complex (ACSC)-induced cell proliferation.

10 Claims, 6 Drawing Sheets

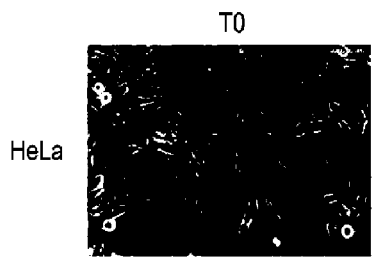
FIG. 1A
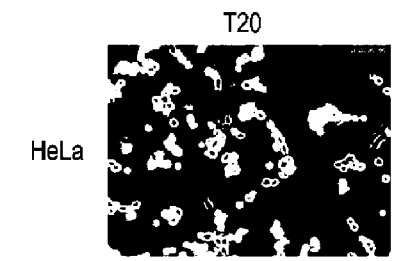
FIG. 1B
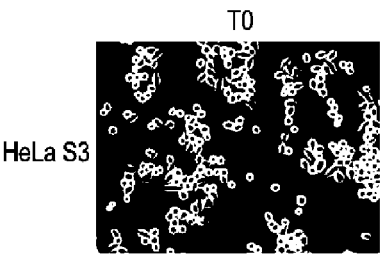
FIG. 1C
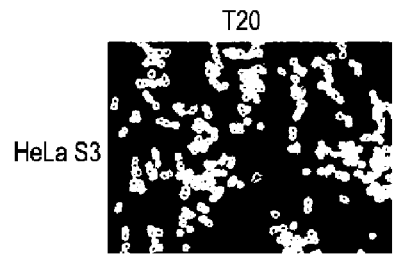
FIG. 1D
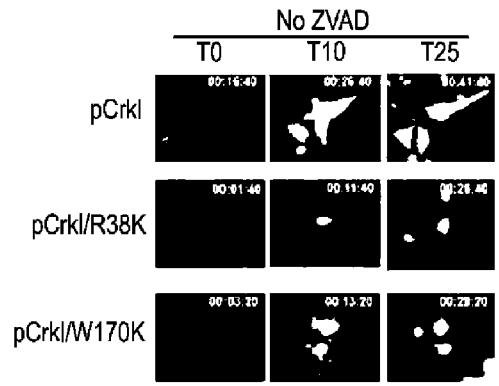
FIG. 2A
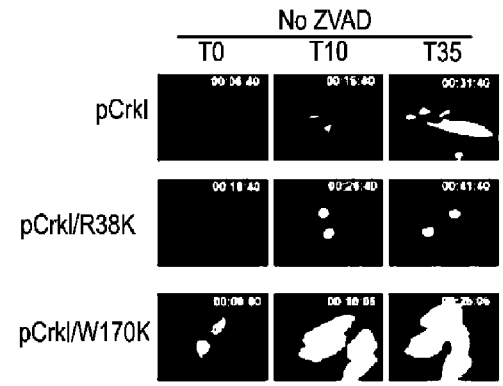
FIG. 2B
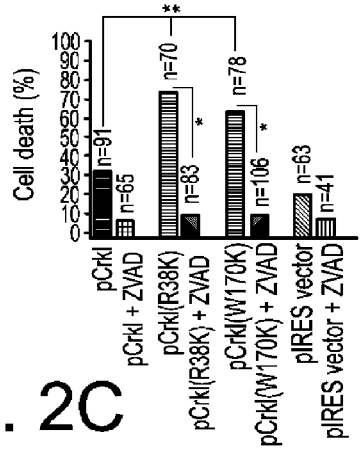
FIG. 2C
| Gene | Time to death (hrs) |
|---|---|
| pExoT | 8.5±1.3; (n=140) |
| pExoT(G-A+) | 8.6±0.8; (n=58) |
| pExoT(G+A-) | 16.2±1.3; (n=62) |
| pR38K | 9.2±1.0; (n=35) |
| pW170K | 11.2±1.3; (n=35) |
FIG. 2D

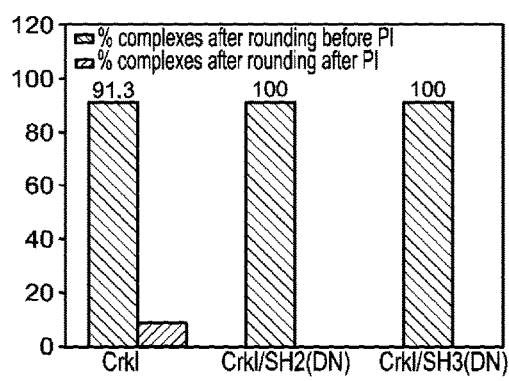
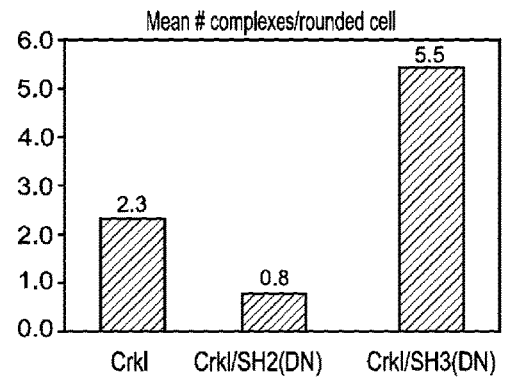
FIG. 4    FIG. 5
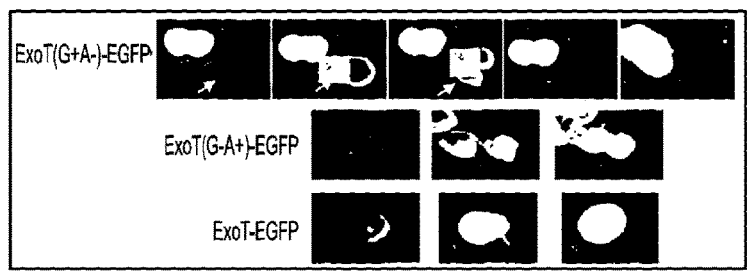
FIG. 6A
FIG. 6B
FIG. 6C
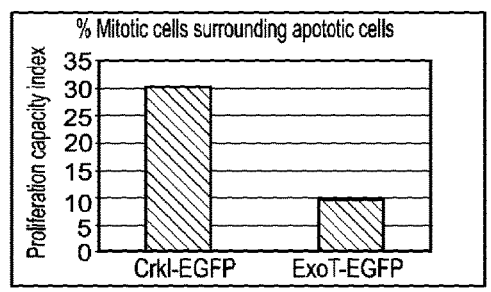
FIG. 7

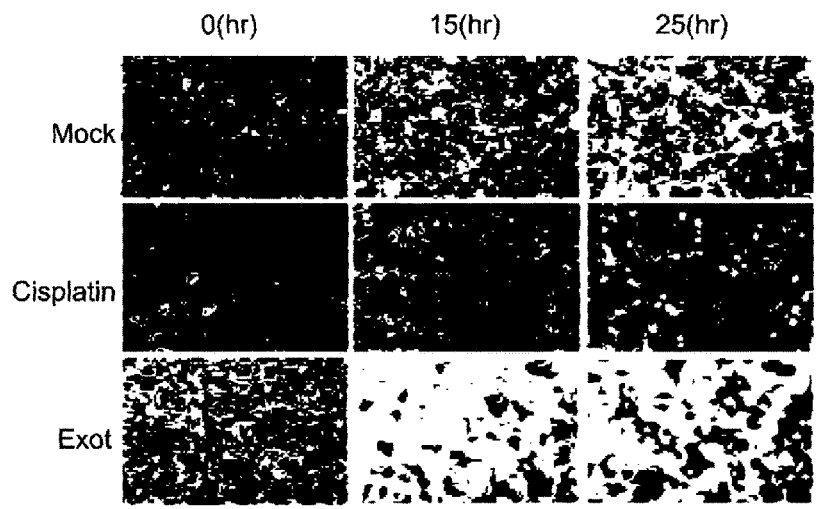
FIG. 8A
FIG. 8B
FIG. 8C
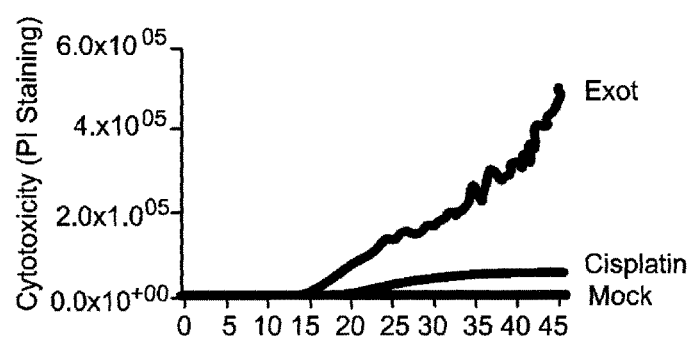
FIG. 8D

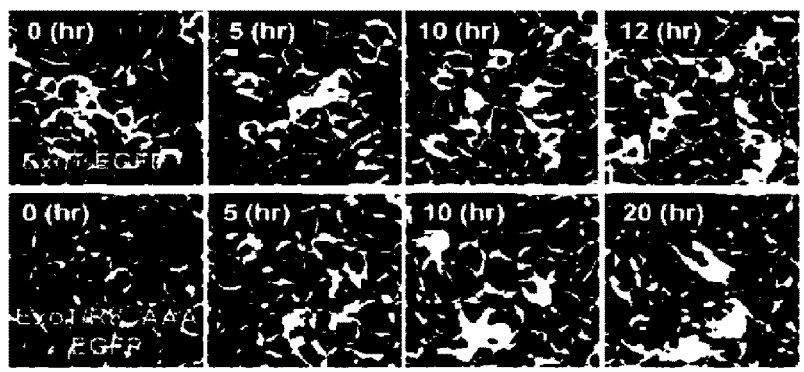
FIG. 8E
FIG. 8F
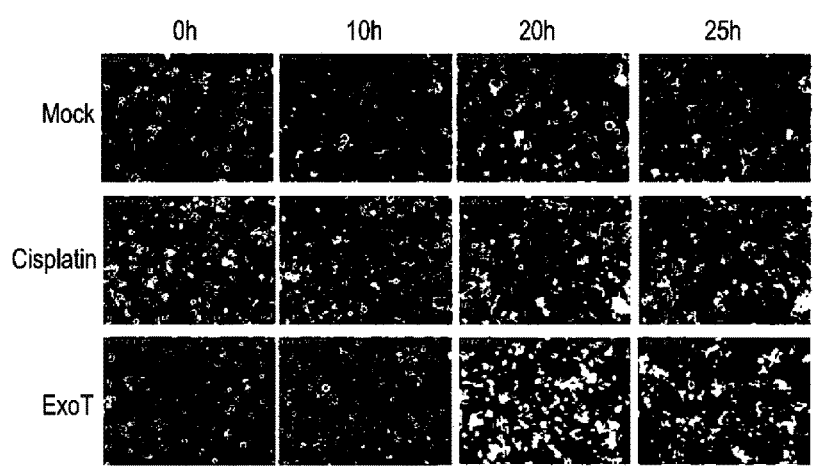
FIG. 9A
FIG. 9B
FIG. 9C

CRK—A NOVEL TARGET FOR CANCER THERAPY

CROSS REFERENCE TO RELATED APPLICATIONS

This application is a divisional of U.S. application Ser. No. 14/008,032, filed Oct. 15, 2013, which is the U.S. National Stage of International Application No. PCT/US2012/031470, filed on Mar. 30, 2012 and published in English, which claims the benefit of U.S. Provisional Application Ser. No. 61/469,861, filed on Mar. 31, 2011, the entire teachings of which are incorporated herein by reference.

TECHNICAL FIELD

This disclosure relates generally to Crk-based compensatory proliferation pathway as a target for cancer therapy. More specifically, this disclosure assesses the potential of Crk protein as a target for cancer treatment by dissecting its role as a scaffold for ACSC and its inhibition by the ExoT toxin. This should lead to a new class of anti cancer drugs, one whose function is to prevent the compensatory proliferation complexes generated by cancer cells in response to therapy, thus enhancing the efficacy of cancer treatment by traditional cancer drugs.

BACKGROUND

Approximately one million cells die every second in the course of normal tissue turnover in humans through apoptosis, a highly regulated process of programmed cell death (PCD). Cell death must swiftly and accurately be balanced with compensatory proliferation to maintain homeostasis and tissue integrity. Apoptosis, in addition to its role in cellular demise, has also been implicated in triggering homeostatic compensatory proliferation, whereby dying cells are thought to induce proliferation in their neighboring cells as a means to control cell number. The molecular components of apoptotic compensatory proliferation signaling and the underlying mechanism of compensatory proliferation remain unknown.

Promoting apoptosis has long been used as a main strategy for cancer drug discovery. Many cancer drugs induce apoptosis in cancer cells but frequently fail to eradicate solid tumors. The failure to eradicate particularly large tumors may be in large part due to this compensatory proliferation signaling mechanism. Understanding these natural mechanisms of compensatory proliferation has a profound therapeutic implication for cancer.

SUMMARY OF THE DISCLOSURE

*Pseudomonas aeruginosa* (PA) is one of the most virulent bacterial pathogens of humans that thrives in injured tissues and has evolved mechanisms to inhibit wound healing. This disclosure demonstrates that PA actively inhibits wound healing by injecting Exotoxin T (ExoT) virulence factor directly into target host cells where it inhibits cell division by targeting cytokinesis and induces apoptosis in its target host by distinct mechanisms. This disclosure identifies a novel apoptotic compensatory proliferation signaling complex (ASCS) involving ExoT's cellular target, CrkI. This disclosure demonstrates that in cells induced to undergo apoptosis, CrkI forms globular complexes which associate with plasma membrane in the apoptotic cell and are released from the dying cell to its healthy neighbor, inducing it to proliferate. In accordance with this disclosure, ExoT is administered to prevent the ACSC assembly while inducing apoptosis, indicating that apoptotic program cell death and compensatory proliferation may be distinct and may be uncoupled from each other.

Without being bound to any particular theory, it is believed that CrkI functions as a scaffold for the ACSC assembly and that its ADP-ribosylation by ExoT interferes with this process while resulting in anoikis apoptotic cell death.

Toxins are employed as molecular tools to dissect animal cellular processes. The molecular mechanisms that underlie cytotoxicity induced by *Pseudomonas aeruginosa* toxins in their target host cells have been studied. While investigating the molecular mechanism that underlies a *Pseudomonas aeruginosa* ExoT toxin, to induce apoptosis, a novel signaling complex has been identified and which will be referred to as apoptotic compensatory signaling complex (ACSC), involving the ExoT's cellular target, Crk. It has been discovered that CrkI functions as a scaffold for the assembly of the ACSC and that *Pseudomonas aeruginosa* ExoT interferes with ACSC formation while inducing potent apoptosis. This discovery is highly significant on multiple levels. This is a novel cell-cell signaling mechanism that has not been previously described. Moreover, it has important implications in cancer biology and treatment. Promoting apoptosis has long been used as a main strategy for cancer drug discovery (Fesik, 2005). Many cancer drugs, such as taxol, tamoxifen, hydroxyurea, and camptothecin, destroy cancer cells by inducing apoptosis but frequently fail to eradicate large tumors. Undoubtedly, this failure is at least in part due this apoptotic compensatory proliferation signaling. Importantly, it has been demonstrated that ExoT, by targeting Crk, induces potent apoptosis in cancerous cells while blocking their ability to generate ACSC-mediated proliferation signaling. Without being bound to any particular theory, this indicates that apoptotic PCD and apoptotic compensatory proliferation signaling may be distinct and may be uncoupled from each other, thus, making the Crk-based compensatory proliferation pathway highly attractive as a target for cancer therapy.

It is believed that the failure to eradicate large tumors by cancer drugs is at least partly explained by ACSC-mediated proliferation signaling. This disclosure demonstrates that as cancer cells succumb to apoptosis, they are promoting proliferation in their surrounding cells, thus reducing the efficacy of treatment. Moreover, an ACSC-producing cell could potentially disrupt normal tissues by inducing non-dividing normal cells in a tissue to lose contact with other cells while undergoing mitosis. This would create an opportunity for cancer cells to invade tissues, thus enhancing metastasis. It is proposed herein that drugs that block and/or inactivate the Crk-based proliferation complexes would enhance the efficacy of the traditional cancer therapy and substantially improve the desired outcome, which is tumor eradication.

BRIEF DESCRIPTION OF THE DRAWINGS

FIGS. 1A-1D shows four photographs illustrating that ExoT appears to induce Anoikis PCD. Anoikis-sensitive (HeLa) or Anoikis-resistant (HeLa S3) cells were infected with the ExoT-expressing PA strain (PA103 AU) at an MOI of ca. 10. Host cell death was assessed by uptake of propidium iodide (PI) by simultaneous time lapse phase and fluorescent video microscopy. Video images were captured every 15 min. Representative frames are shown.

FIGS. 2A-2D illustrate photographically, graphically and in a chart that transient transfection of DN Crk induces cell death in HeLa cells. Specifically, HeLa cells were transiently transfected with wild type CrkI (pCrkI), SH2 DN (pCrkI/R38K), or SH3 DN (pCrkI/W170K) fused to C FP in the absence (FIG. 2A) or presence (FIG. 2B) of carbobenzoxy-valyl-alanyl-aspartyl-[O-methyl], or ZVAD. PI was added to identify dying calls and cell death was analyzed by time-lapse video microscopy, as shown in FIG. 2C. The tabulated results shown in FIG. 2D, were collected from multiple videos. The time to death was defined as the time of expression of transfected gene (appearance of green) to the time of PI uptake (appearance of yellow) and expressed as the mean+SEM.

FIG. 4 graphically illustrates that ACSC formation is an active process. Specifically, the incidence of apoptotic compensatory signaling complex (ACSC) release from CrkI, CrkI-R38K (SH2 DN), and CrkI-VV170K (SH3 DN) transfected HeLa cells is shown in bar chart form.

FIG. 5 graphically illustrates that ACSC formation is regulated differently by SH2 and SH3 domains. Specifically, the number of ACSC complexes per apoptotic CrkI, CrkI (SH2 DN), and CrkI (SH3 DN) transfected HeLa cells was determined and the results are presented in bar chart form.

FIGS. 6A-6C photographically illustrate that the ADPRT domain of ExoT appears to inhibit ACSC. Specifically, as shown in FIG. 6A, the ExoT(G+A−)-EGFP tags along with the ACSC but does not interfere with its activity to induce proliferation in the recipient cell. As shown in FIGS. 6B and 6C, no ACSC-like globular complexes were observed in the ExoT-EGFP (FIG. 6C) or the ExoT(G−A+)-EGFP (FIG. 6B) transfected cells, suggesting that the ADPRT domain of ExoT may inhibit ACSC assembly.

FIG. 7 graphically illustrates that ExoT blocks ACSC-induced proliferation in surrounding cells. Specifically, the proliferation capacity index of the CrkI-EGFP or ExoTE-GFP transfected apoptotic cells was defined based on the capacity to induce proliferation in the neighboring cells within six hours after cell rounding.

FIGS. 8A-8F photographically and graphically illustrate that *Pseudomonas aeruginosa* ExoT induces potent cytotoxicity in B16 melanoma cells. Specifically, FIGS. 8A-8C are photographs of B16 cells infected with *Pseudomonas aeruginosa* strains expressing ExoT or defective in ExoT (Mock) at a multiplicity of infection (MOI) 10 or treated with 50 μM cisplatinum. Cytotoxicity was determined by measuring propidium iodide (PI) staining using immunofluorescent time lapse microscopy. FIG. 8D graphically illustrates the level of cell death, for the samples of FIGS. 8A-8C as indicated by PI staining intensity in pixels as measured from each frame using NIH Image J software. FIGS. 8E-8F photographically illustrate B16 cells that were transiently transfected with pIRES expression vectors harboring ExoT-EGFP or its inactive form, (ExoT/RK, AAA)-EGFP.

FIGS. 9A-9D illustrate that *Pseudomonas aeruginosa* ExoT is a potent inducer of cell death in 4T1 metastatic breast tumor cells. Specifically, in FIGS. 9A-9C, 4T1 cells were infected with PA103 strains expressing ExoT or defective in ExoT expression (Mock), or treated with 50 μM cisplatinum (Cisplatin). FIG. 9D graphically illustrates the cytotoxicity which was determined by propidium iodide (PI) staining using immunofluorescent timelapse microscopy, which illustrates that these toxins or cisplatin kill 4T1 cells with different potency and kinetics.

DETAILED DESCRIPTION

Figure 3A:
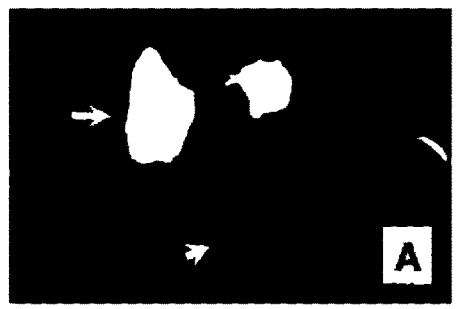
FIGS. 3A-3F shows six photographs sequentially illustrating the apoptotic compensatory signaling complex (ACSC). Specifically, HeLa cells were transiently transfected with CrkI-GFP expression vector. CrkI forms complexes (indicated bHeLa cells were transiently transfected with CrkI-GFP expression vector. CrkI forms complexes (indicated by white arrows) which go through a cytoplasmic bridge from a dying cell (indicated by red arrow) and induce healthy neighbor recipient cells (indicated by yellow arrow) to divide. Six frames (FIGS. 3A-3F) from IF timelapse microscopy are shown.
Figure 3D:
Figure 3B:
Figure 3E:
Figure 3C:
Figure 3F:

Although, the concept of apoptotic compensatory proliferation was first recognized over 30 years ago and has been intently pursued in recent years by several groups studying eye and wing tissue development in *Drosophila melanogaster*, the molecular components of apoptotic compensatory signaling complex (ACSC), the nature of signaling, and the underlying mechanism of compensatory proliferation remain largely unknown. This disclosure identifies a pivotal component of compensatory proliferation and provides an assay to test for its activity.

Currently, there are no drugs in the market developed to prevent the compensatory proliferation signaling emitted from dying cancer cells. Targeting Crk for cancer therapy is a novel approach for it enables us to paralyze this proliferation signaling, thus enhancing the efficacy of cancer treatments by other apoptosis-inducing traditional cancer drugs.

In this disclosure, the role of CrkI as a scaffold for the ACSC assembly and the characterization its mode of function are explained. Transient transfection of HeLa cells with cellular CrkI expression vector resulted in 32% apoptosis. In the CrkI-transfected apoptotic cells, CrkI formed globular complexes which associated with the plasma membrane and were released from the apoptotic but viable cells to healthy neighboring cells, inducing them to proliferate upon contact. A dominant negative (DN) mutation in the Src Homology domain 2 (SH2) of CrkI significantly reduced the ACSC assembly, whereas, a DN mutation in the SH3 domain of CrkI substantially enhanced the ACSC formation and release. Without being bound to any particular theory, it is believed that CrkI functions as a scaffold for the ACSC assembly in a manner that is dependent on its SH2 domain interactions. We also hypothesize that CrkI SH3 domain interactions regulate the frequency and the incidence of the ACSC formation and release from the apoptotic cells. The molecular events that occur specifically in the apoptotic (donor) cells with respect to the ACSC formation and release were studied. Constitutive or inducible stable cell lines harboring CrkI-GFP or YFP will be constructed and used as donor or recipient cells respectively. The donor cells will be subjected to various treatments. The treated cells will then be mixed with the untreated YFP-expressing recipient cells in a 1:3 or 1:4 ratios and the ACSC formation, release, and activity will be assessed by time-lapse IF video microscopy.

This disclosure provides answers to the following questions: (i) What types of program cell death trigger ACSC formation? (ii) What is the role of caspases in the ACSC formation and/or its function? And (iii) what are the specific roles of the SH2 and SH3 domains of CrkI with respect to ACSC assembly, release, and regulation?

To test the hypothesis that the ExoT's ADP-ribosylation of Crk leads to anoikis apoptotic cell death and interferes with Crk's function as a scaffold for the ACSC assembly, cells intoxicated with ExoT underwent cell shrinkage and detachment from the surface prior to cellular demise, phenotypically resembling the anoikis PCD. ExoT also appears to interfere with the Crk-based ACS complex assembly. ExoT ADP-ribosylates CrkI and CrkII focal adhesion proteins and interferes with their activity. Expression of CrkI SH2 or SH3 dominant negative (DN) mutations phenocopy the ExoT-mediated cytotoxicity. These data provide the rationale for the stated hypothesis that cellular, biochemical, and molecular approaches to dissect the mechanism(s) that underlies the ExoT-mediated apoptosis and its inhibition of compensatory proliferation signaling.

In addition to its role in cellular demise, apoptosis has been implicated in triggering homeostatic compensatory proliferation, whereby dying cells are thought to induce proliferation in their neighboring cells as a means to control cell number. The molecular components of ACSC, the nature of signaling, and the underlying mechanism of compensatory proliferation remain unknown. Promoting apoptosis has been used as a main strategy for cancer drug discovery. Many cancer drugs, such as taxol, tamoxifen, hydroxyurea, and camptothecin, destroy cancer cells by inducing apoptosis but frequently fail to eradicate large tumors. Undoubtedly, this failure is at least in part, due this apoptotic compensatory proliferation signaling. Understanding these natural mechanisms of compensatory proliferation has a profound therapeutic implication for cancer.

This disclosure shows that CrkI functions as a scaffold for the assembly of the ACSC is significant on multiple levels. (i) This is a novel cell-cell signaling mechanism that has not been described previously. (ii) It has important implications in cancer biology and therapy. (iii) The finding that ExoT can induce apoptosis while blocking the ACSC signaling indicates that apoptotic PCD and apoptotic compensatory proliferation signaling are distinct and can be uncoupled from each other, thus, making this pathway highly attractive as a target for cancer therapy. And (iv) data emerging from the proposed studies in this grant application will no doubt advance our knowledge of *Pseudomonas aeruginosa* (PA) pathogenesis.

PA is one of the most virulent bacterial pathogens. Despite aggressive antibiotic therapy, the fatality rate amongst individuals with PA infection is extremely high, due to the high intrinsic resistance of PA to many antibiotics and the emergence of multi-drug resistant strains. Novel therapeutic approaches are urgently needed to prevent and treat PA infections.

Besides their critical role in the pathogenesis of infectious diseases, microbial toxins provide an extensive set of reagents and clues for research in various scientific disciplines. As cellular microbiologists, our approach is to apply the knowledge gained from studying pathogens toward advancing our understanding of host cellular processes. This application is highly innovative because it incorporates multiple scientific disciplines, including bacterial pathogenesis, cell biology, and cancer biology. The existence of a novel protein based cell-cell communication complex (ACSC) that mediates the apoptotic compensatory signaling is revealed.

The ACSC-mediated signaling is the most efficient way to maintain homeostasis and tissue integrity as it ensures a rapid and controlled local proliferation response to account for cell loss during injury and cellular damage. The failure to eradicate large tumors by cancer drugs is at least partly explained by the ACSC signaling. This disclosure demonstrates that as cancer cells succumb to apoptosis, they are promoting proliferation in their surrounding cells, thus reducing the efficacy of treatment. Moreover, an ACSC-producing cell could potentially disrupt normal tissues by inducing non-dividing normal cells in a tissue to lose contact with other cells while undergoing mitosis. This would create an opportunity for cancer cells to invade tissues, thus enhancing metastasis. The donor and the recipient cells will be separated in order to directly examine the molecular events that occur in each cell type during ACSC signaling.

PA requires and thrives in wounds and has evolved virulence mechanisms to inhibit wound healing. In particular, Exotoxin T (ExoT) plays a pivotal role in the inhibition of wound healing by PA. ExoT is a bifunctional toxin possessing a GTPase Activating Protein (GAP) domain at its N-terminus and an ADP-ribosyltransferase (ADPRT) domain at its C-terminus. ExoT contributes to the inhibition of wound healing by two novel and distinct virulence functions: (i) It blocks host cell division by targeting cytokinesis at multiple steps and (ii) it prevents pro-inflammatory necrotic cytotoxicity while re-routing its target host toward silent apoptotic demise (data not shown). The mechanisms by which ExoT exerts these two activities remain largely undetermined.

Is demonstrated that ExoT is both necessary and sufficient to induce apoptosis in target host epithelium and that ExoT-mediated cytotoxicity is primarily dependent on its ADP-ribosyl transferase (as being ADPRT) domain activity, although the GAP domain also contributes. HeLa cells, intoxicated with ExoT, displayed cell rounding and detachment from the surface prior to cell death (data not shown), morphologically resembling anoikis apoptotic PCD which ensues when cells lose connection with the substratum and/or when they engage in inappropriate interactions with extracellular matrix. CrkI and CrkII focal adhesion proteins are the primary targets of ExoT ADPRT activity. It is hypothesized that ExoT's ADP-ribosylation of Crk proteins results in focal adhesion disassembly and anoikis cell death. Interestingly, Crk adaptor proteins have been implicated in cell death, although their role in cytotoxicity remains controversial. In a *Xenopus* egg extract model system for apoptosis, addition of cellular Crk leads to cell death, while Crk immunodepletion or expression of its SH2 or SH3 dominant negative (DN) forms, protect against cytotoxicity. On the other hand, Cho et al. have demonstrated that disruption of cell migration by SH2 or SH3 DN forms of Crk prevented Crk interaction with p130Cas and resulted in cell death in COS-7 cell line. If ExoT induces anoikis PCD, the anoikis-resistant cells should be also resistant to the ExoT-mediated cytotoxicity. Unlike HeLa cells which undergo anoikis apoptosis upon detachment from the substratum, HeLa-S3 cells (ATCC #: CCL-2.2) are resistant to anoikis and have been adapted to grow both as adherent cells on the surface and as non-adherent cells in suspension media.

To test this hypothesis, $1\times10^5$ HeLa and HeLa-S3 cells were infected with ExoT-expressing PA103 strain at MOI of about 10 and assessed apoptosis by immunofluorescent (IF) video microscopy in the presence of propidium iodide (PI) as described. As shown in FIG. 1, HeLa-S3 cells were resistant to the ExoT-induced cytotoxicity.

Dominant negative (DN) mutations in SH2 and SH3 domains of CrkI have been shown to interfere with known cellular activities of both CrkI and CrkII. We postulated that if modification of Crk by ExoT is responsible for inducing anoikis, DN mutations in CrkI domains might also result in apoptosis, phenocopying the ExoT's cytotoxicity. To investigate this hypothesis, HeLa cells were transfected with mammalian expression vectors harboring CrkI or its SH2 (CrkI/R38K) or SH3 (CrkI/W170K) DN mutant forms, fused at their C-termini to GFP, and assessed apoptosis by IF video microscopy in the presence or absence of Z-VAD, a pancaspase inhibitor that blocks known apoptotic cell deaths. As shown in FIG. 2, expression of CrkI SH2 or SH3 DN forms substantially increased Z-VAD-sensitive apoptosis in HeLa cells {about 80% for SH2 mutant (n=80) and about 70% for SH3 (n=78); p<0.001, compared to only 10% cell death which occurred upon transfection with the control vector (n=98)}. Expression of wild type CrkI also increased apoptosis, albeit to a lesser extent (about 32%, n=91, p<0.01). Also of note, the time to death in the presence Crk or its SH2 or SH3 DN forms were also very similar to the observed time to death in the presence of ExoT or ExoT with functional ADPRT, ExoT(G−A+) (FIG. 2D), supporting the notion that ExoT-mediated cell death likely involves Crk.

CrkI is a component of apoptotic compensatory signaling complex (ACSC). The concept of compensatory proliferation was first recognized over 30 years ago. Several recent studies involving eye and wing tissue development in *Drosophila melanogaster* have established the link between apoptotic PCD and apoptotic compensatory proliferation. However, the molecular components of apoptotic compensatory signaling complex, the nature of signaling, and the underlying mechanism of compensatory proliferation remain largely unknown.

During the transient transfection studies described above, it was observed that in over 60% of the CrkI-GFP transfected apoptotic cells, CrkI-GFP formed globular complexes which associated with plasma membrane and were released from the apoptotic but viable cells, (defined by cell shrinkage but PI negative), to healthy neighboring cells (defined by spread-out morphology), inducing them to proliferate upon contact (FIGS. 3-4). The Nomenclature Committee on Cell Death (NCCD) has recently defined nuclear staining by PI as an irreversible "point-of-no-return" step which signifies death. This important observation suggested that CrkI adaptor protein may be a component of the apoptotic compensatory signaling complex (ACSC). The SH2 mutant (CrkI/R38K-GFP) also formed ACSC complexes but in substantially fewer transfected apoptotic cells (20%) and at a significantly reduced frequency (0.8 complex/ACSC producer cell, compared to 2.3 complexes in CrkI), suggesting that SH2 domain interactions may be necessary for the ACSC assembly (FIG. 5 and data not shown). Conversely, the SH3 mutant (CrkI/W170K-GFP) formed ACSC complexes in significantly larger number of transfected apoptotic cells (about 80%) and at a much higher frequency (5.5 complex/ACSC producer cell), suggesting that ACSC formation may be negatively regulated by the SH3 domain interactions. ASCS complexes were not observed in healthy transfected cells nor were they seen in apoptotic cells after they succumbed to death (became PI positive), indicating that ACSC assembly and release occurs in apoptotic but viable cells (FIG. 4). Regardless of the type of CrkI (wild type, SH2 DN, or SH3 DN) in the complex, 100% of recipient cells underwent cell division within one to six h, compared to only about 12% cell division that occurred in nearby cells which did not make contact with these complexes within the same time frame, indicating that these complexes promote proliferation in the recipient cells (data not shown).

ExoT inhibits ASCS formation. Although, the ExoT-induced apoptosis is primarily due to its ADPRT domain activity, the GAP domain can also induce apoptosis but with significantly reduced potency (only 50% cell death, compared to 100% apoptosis induced by ExoT or its ADPRT domain) and much longer kinetics (FIG. 2D). As shown in FIGS. 6A-6C, HeLa cells, which were induced to undergo apoptosis by transfection with the functional GAP but mutant ADPRT expression vector, pExoT(G+A−)-GFP, the ExoT(G+A−)-GFP toxin formed small globular complexes that moved from the apoptotic cells to neighboring cells, similar to the ACSC, suggesting that ExoT(G+A−) toxin interacts with the ACSC complexes. Despite inducing apoptotic cytotoxicity in 100% of transfected HeLa cells, these complexes were never observed in the ExoT-EGFP (FIG. 6C) or the ExoT(G−A+)-GFP (FIG. 6B) transfected apoptotic HeLa cells. This data suggests that the ADPRT activity may interfere with the ACSC assembly. This finding is consistent with the critical role of the SH2 domain of CrkI in the ACSC assembly (FIG. 5) as the ExoT ADP-ribosylation of CrkI has been shown to interfere with the ability of the SH2 domain of Crk to interact with other proteins, including paxillin and p130Cas. If ExoT inhibited ACSC assembly and signaling, it was reasoned that there should be a reduction in the number of mitotic cells surrounding the ExoT-induced apoptotic cells. We assessed the proliferation capacity index associated with ExoT- or CrkI apoptotic cells. Consistent with this hypothesis, a substantial reduction in the percentage of mitotic cells surrounding the ExoT-transfected apoptotic HeLa cells occurred compared to the CrkI-transfected apoptotic cells (FIG. 7). These data have important implication on cancer therapy as they indicate that the apoptotic PCD and apoptotic proliferation signaling are distinct and can be uncoupled from each other. Without being bound to any particular theory, it is believed that CrkI adaptor protein functions as a scaffold for the ACSC assembly and that PA utilizes ExoT to block this process while inducing apoptosis in its target host.

The general approach is to separate the donor and the recipient cell populations to dissect the molecular events that underlie the ACSC formation in donor cells and distinguish them from the proliferation signaling that takes place in the recipient cells. 70% of CrkI-EGFP-transfected HeLa cells did not undergo apoptosis and remained viable throughout these studies as shown in FIGS. 2A-2D, suggesting use of CrkI-EGFP as a marker for the ACSC in donor cell population. Constitutive and inducible stable cell lines in HeLa cells were used for expressing CrkI-EGFP (donor cells) or Yellow fluorescent protein (YFP) as a marker for the recipient cells. The inducible stable donor or recipient cell lines will be constructed using Clontech's pTetOn system, according to the manufacturer's guidelines. Plasmids harboring the CrkI-EGFP or the EGFP control in the pTRE2hyg response vector (Clontech #631014) were constructed. Briefly, the pTetOn HeLa cells (Clonetch, #630901) will be seeded 24 h prior to transfection at $10^5$ cells/well in a 6 well plate. When the cells are about 80% confluent, they will be co-transfected with pTet-tTS vector, (Clontech #630901) which prevents low-level background expression, and pTRE2hyg::crkI-egfp, pTRE2hyg::egfp, or pTRE2hyg::yfp in a 10:1 ratio using Effectene® transfection reagent (Qiagen #301425) according to the manufacturer's guidelines. 24 h post transfection, the cells will be passaged into 60 mm dishes and put in selection media containing hygromycin B. Media will be changed every 2 days and plates will be monitored for the formation of colonies. Colonies will be isolated and checked for doxycycline induced expression to ensure that CrkI-mediated cytotoxicity does not occur in these cell lines. The constitutive stable donor or recipient cell lines will be constructed by transfecting HeLa cells with pCrkI-EGFP, pEGFP, or pYFP (constructed in modified pIRES2-EGFP expression vector, FIG. 2). Selection for the constitutive stable cell lines will be for G418. The donor and the recipient cells will be separately subjected to various treatments, as described in Specific Aims below. After treatment, donor and recipient cells will be mixed in a 1:3 or 1:4 (Donor: Recipient) ratios, seeded, and the ACSC formation, release, and signaling will be analyzed by IF time-lapse video microscopy and/or flow cytometry. This approach will allow us to separate the donor and the recipient cell populations and address specific questions in regard to the molecular events that lead to the ASCS formation and release in the donor cells, on a single cell-based analyses.

What types of PCD trigger the ACSC formation? Programmed cell death can be broadly divided into two categories, apoptosis and necrosis/oncosis. Apoptosis involves the sequential activation of a cascade of proteases called initiator and effector caspases and is further divided into intrinsic and extrinsic pathways. The intrinsic apoptosis proceeds through the mitochondria pathway and requires the activation of the initiator caspase-9 which in turn triggers the processing and activation of effector caspases-3 and -7, culminating in apoptotic cell death. In the extrinsic pathway, death ensues as a consequence of death ligands, such as FasL, activating their respective death receptors, such as Fas. Activation of the extrinsic pathway then leads to the recruitment of and the activation of the initiator caspase-8, which ultimately activates effector caspases-3 and -6, leading to the apoptosis. Both the intrinsic and the extrinsic pathways are effectively blocked by the pancaspase inhibitor Z-VAD-fmk. The caspase-independent necrotic/oncotic mode of programmed cell death is associated with severe cellular trauma, such as membrane damage, and is poorly defined at the mechanistic level. Whether the compensatory proliferation signaling occurs only in response to apoptotic PCD or if necrotic cells can also signal their own demise remains unknown. It is also unclear whether or not all apoptotic PCD can trigger compensatory proliferation signaling. To address these questions, donor cells will be treated for 2, 4, and 6 hours with stimuli, known to induce various apoptotic or non-apoptotic PCD, including camptothecin which triggers the intrinsic pathway (4 µM final concentration), TNFα/cycloheximide which induce the extrinsic pathway (10 ng/ml and 1 µg/ml respectively), ionizing radiation which triggers the anoikis apoptotic pathway, and 0.1% $H_2O_2$ which induces necrotic cytotoxicity. After treatment, donor and recipient cells will be mixed in a 1:3 or 1:4 ratios respectively, seeded, and the ACSC formation, release, and signaling may be analyzed by IF time-lapse video microscopy, as shown in FIGS. 2A-2D.

Regarding the role of caspases in the ACSC formation, recent studies involving eye and wing tissue development in *Drosophila melanogaster* have demonstrated that Drone initiator or DrICE effector caspases may be required for this process, thus linking the process of cellular demise to signaling for compensatory proliferation. Other studies, however, have disputed the importance of at least the initiator caspase Drunc in this process. In our studies treatment with a broad inhibitor of apoptosis, Z-VAD. completely blocked ACSC formation under all conditions but it also blocked apoptotic PCD (data not shown). Whether caspases directly partake in the ASCS assembly and/or signaling, independent of their role in PCD, or indirectly via inducing PCD remains unclear. Initially, the focus was placed on the initiator caspases 8 and 9 and the effector caspase-3 for their possible role in ASCS signaling because they are the caspases involved in the major apoptotic PCD, namely the extrinsic and the intrinsic PCD respectively. The donor cells will be treated with camptothecin or TNFα/ cycloheximide, as described in Aim 1.1, in the presence of Z-LEHD-fmk (caspase-9 inhibitor), Z-IETD-fmk (caspase-8 inhibitor), Z-DEVD-fmk (caspase-3 inhibitor), or Z-LEHD-fmk plus Z-IETD-fmk mixture. Caspase-inhibitors will be purchased from RandD Systems and added at 60 µM final concentration at either 2 hrs prior or 4 hrs after addition of the inducers of apoptosis and will be maintained throughout afterwards. These time points were chosen based on the kinetics of apoptotic PCD initiation and the ACSC assembly which occurs after cell rounding as determined by microscopy (data not shown). Again, treated donor cells will be mixed with untreated recipient cells and the role of each caspase in the ACSC assembly will be assessed systematically by IF video microscopy. If caspase-9 is required for the ACSC formation, independent of its role in apoptosis, when added 2 hrs prior to camptothecin, it was expected that caspase-9 inhibitor (Z-LEHD-fmk) to inhibit both apoptotic PCD and proliferation signaling in the camptothecin-treated donor cells. When added 5 hrs after camptothecin however, Z-LEHD-fmk should primarily block the ACSC formation but should have little impact on the apoptotic PCD. If caspase-9 is required for the ACSC assembly, regardless of the apoptotic PCD, then Z-LEHD-fmk should also abrogate the ACSC formation and signaling in donor cells treated with the TNFα/cycloheximide while being ineffective in preventing the apoptotic PCD induced by this treatment. However, if caspases 8 and 9 function redundantly to mediate the ASCS formation, then only the mixture of Z-LEHD-fmk and LEHD-fmk would be able to inhibit the ACSC formation, when added 5 hrs after death inducers, while having little effect on apoptotic PCD. The same logic will be used to assess the role of caspase-8 and caspase-3 in the ASCS-mediated signaling.

To dissect the role of the SH2 and SH3 domains of CrkI in regulating the ACSC formation and release, the data indicates that the ACSC assembly and release requires the SH2 domain activity but is negatively regulated by the SH3 domain interactions (FIG. 5 and data not shown). We will extend these studies to gain further insights into the role of SH2 and SH3 domains in the ACSC-mediated signaling. HeLa cells will be transiently transfected with pCrkI/R38K-EGFP (SH2 DN) or pCrkI/W170K-EGFP (SH3 DN) as described in FIG. 2 and the proliferation capacity of apoptotic cells will be determined by counting the number of mitotic cells surrounding the transfected apoptotic cells within 6 hrs after their cell shrinkage by IF video microscopy, as described in FIG. 7. It is expected an increase in the number of mitotic cells in the vicinity of the CrkI/SH3 (DN)-EGFP transfected apoptotic cells and a decrease around the CrkI/SH2 (DN)-EGFP transfected cells. To address the importance of the linkage between the SH2 and the SH3 domain modules with respect to the regulation of the ACSC assembly and release, truncated versions of CrkI: (CrkI SH2-EGFP and CrkI SH3-EGFP), and their respective mutant forms, (CrkI SH2/R38K-EGFP and CrkI SH3/ W170K-EGFP), were constructed and their activity assessed with respect to apoptotic cytotoxicity and the regulation of ACSC assembly and release by time-lapse IF video microscopy as described in FIGS. 2A-2B and 3A-3F.

Through these studies, (i) the type of program cell death that triggers compensatory proliferation signaling, (ii) the role of caspases in this cellular event, and (iii) to delineate the functions of the SH2 and the SH3 domains of CrkI with respect to the regulation of the ACSC assembly and proliferation signaling was determined.

Although, caspase inhibitors have been developed to be specific toward their substrates, they can potentially interfere with the activity of other caspases, complicating the interpretation of the data in Aim 1.2. We will validate our findings by RNA interference gene silencing and protein knockdown technology. Small interfering RNA (siRNA) against all caspases are commercially available (Santa Cruz Biotechnology). Donor cells will be treated with siRNAs against the indicated caspases for 48 hrs prior to the induction of cell death. The efficacy of treatments will be determined by Western blotting. Another potential problem is the construction of the constitutively expressing CrkI-EGFP stable donor cell line, due to Crk's potential cytotoxicity. We will select for stable cell lines and carefully monitor Crk expression in them to ensure that Crk's cytotoxicity does not enter into our studies. Moreover, the doxycyclin-inducible Tet/On stable cell lines will further obviate this concern.

The hypothesis that the ExoT's ADP-ribosylation of Crk SH2 domain leads to anoikis apoptotic cell death and interferes with Crk's function as a scaffold for the ACSC assembly will be tested. As was discussed in Section C-i, our preliminary data suggest that ExoT induces anikis PCD and it also appears to block the ACSC assembly as shown in FIGS. 1A-1D, 6 and 7). Interestingly, expression of CrkI SH2 or SH3 DN mutations also induce apoptosis in HeLa cells, in a manner that phenocopies ExoT as shown in FIGS. 2A-2D. The common hallmarks of anoikis PCD include: down activation of pro-survival signaling molecules Fak, Src, and Akt; enhanced and sustained activation of p38β which is required to drive anoikis demise, by its phoshorylation at Thr180 and Trp182 residues; p130Cas and paxillin degradation; and caspase-3 activation. To investigate whether ExoT/ADPRT cytotoxicity involves anoikis, 105 HeLa cells with ΔU, ΔU/T(G+A−), ΔU/T(G−A+), ΔUΔT, and pscJ::Tn5 (T3SS−) strains (MOI about 10) were infected or transfected with ExoT-EGFP, ExoT(G+A−)-EGFP, ExoT (G−A+)-EGFP, ExoT (G−A−)-EGFP, CrkI-EGFP, CrkI/R38K-EGFP (SH2 DN), CrkI/W170K-EGFP (SH3 DN), or the pIRES-EGFP expression vectors in the presence or absence of Z-LEHD-fmk, Z-IETD-fmk, or Z-LEHD-fmk plus Z-IETD-fmk. Caspase-inhibitors will be added 2 hrs prior to infection or transfection and maintained throughout. The effect of ADPRT or Crk DN expression on Fak, Src, Akt, and p38β activation, and paxillin and p130Cas degradation by Western blot analyses at 1, 3, and 5 hrs post-infection or 15 hrs post-transfection were assessed. Similarly, cell death will be analyzed by IF video microscopy in the presence of PI as described as shown in FIGS. 1A-1D. The effect of ExoT's ADPRT domain activity on the ACSC formation by adding azurin p18 N-terminal fusions with the ExoT, ExoT(G−A+), ExoT(G+A−), ExoT(G−A−), all fused to mCherry at their C-termini, to the donor/recipient mix, 5 hrs after induction of apoptosis in donor cell population was also examined. p18 peptide (amino acids 50 to 67 of azurin) was used to successfully deliver cargo proteins such as GFP into various cell lines including HeLa cells.

It is expected that in the presence of ADPRT or DN Crk mutants: Fak, Src, and Akt activation will be significantly diminished, p38β will become activated, paxillin and p130Cas will be degraded and caspase-3 will become activated. It is also expected to confirm our hypothesis that the ADPRT activity of ExoT inhibits the ASCS assembly.

The studies outlined above are intended to lay foundation for the initial characterization of CrkI protein as a scaffold for the ACSC assembly and the use of ExoT as a tool to uncouple the apoptotic PCD from the proliferation signaling. This disclosure provides a pathway to determine (i) if the ACSC signaling is restricted to transformed cells or whether it also occurs in primary cell lines, as would be expected. (ii) What is the impact of the ACSC signaling on normal tissue structure? (Implication on metastasis). And (iii) what are the components of the apoptotic compensatory signaling complex? Understanding the molecular processes that occur in the recipient cells upon contact with the ASCS may prove useful. The hypothesis that ACSC functions as a preassembled signaling complex which triggers proliferation in the recipient cell by substituting for growth factors will be tested. It is hypothesized that ACSC signaling is mediated by the Crk→Shc→Src/Grb2→Ras→MAPKK→Erk1/2→proliferation pathway in the recipient cell.

FIGS. 8A-8F establish that *Pseudomonas aeruginosa* ExoT induces potent cytotoxicity in B16 melanoma cells. B16 cells were infected with *Pseudomonas aeruginosa* strains expressing ExoT or defective in ExoT (Mock), at multiplicity of infection (MOI) 10 or treated with 50 μM cisplatinum (FIGS. 8A-8C). Cytotoxicity was determined by measuring propidium iodide (PI) staining (red) using immunofluorescent time lapse microscopy. Still images are shown. The level of cell death, indicated by PI staining intensity (pixels), was measured from each frame using NIH Image J software (FIG. 8D). B16 melanoma cells were transiently transfected with pIRES expression vectors, harboring ExoT-EGFP or EGFP alone. Cytotoxicity was determined by PI staining using IF microscopy. B16 cells were transiently transfected with pIRES expression vectors harboring ExoT-EGFP or its inactive form (ExoT/RK, AAA)-EGFP (FIGS. 8E-8F).

Figure 9D:
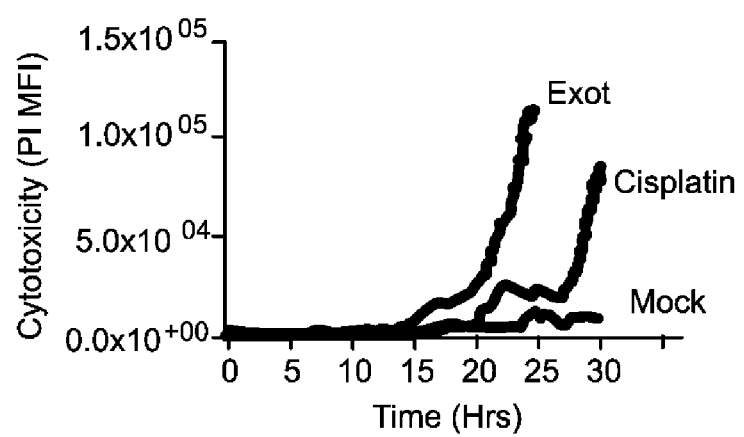

*Pseudomonas aeruginosa* ExoT is a potent inducer of cell death in 4T1 metastatic breast tumor cells as shown in FIGS. 9A-9D. Specifically, 4T1 cells were infected with PA103 strains expressing ExoT (ExoT) (FIG. 9C) or defective in ExoT expression (Mock) (FIG. 9A), or treated with 50 μM cisplatinum (Cisplatin) (FIG. 9C). Cytotoxicity was determined by propidium iodide (PI) staining using immunofluorescent timelapse microscopy (FIG. 9D). Still images are shown in FIGS. 9A-9C and the level of PI stain was measured by Image J. Note that these toxins or cisplatin kill 4T1 cells with different potency and kinetics.

What is claimed is:

1. A method of identifying a therapeutically active compound that inhibits apoptotic compensatory signaling complex (ACSC)-induced cell proliferation, the method comprising:
   providing an in vitro cell population comprising a scaffold for the ACSC-induced cell proliferation;
   adding an apoptosis-inducing agent to the cell population;
   culturing the cell population in the presence of the apoptosis-inducing agent;
   measuring a proliferation capacity index of a portion of the cultured cell population exposed to a test compound;
   measuring a proliferation capacity index of a portion the cultured cell population exposed to a control; and
   wherein a decrease in the proliferation capacity index of the cell population exposed to the test compound, as compared to the proliferation capacity index of the cell population exposed to the control, is indicative of a therapeutically active compound.

2. The method of claim 1, wherein the scaffold comprises a protein selected from the group consisting of Crk, CrkI, CrkI/SH2(DN), CrkI/SH3(DN), and a combination thereof.

3. The method of claim 2, wherein the cells of said cell population comprise an expression vector comprising a nucleotide sequence that encodes the protein.

4. The method of claim 1, wherein the test compound is the same as the apoptosis-inducing agent.

5. The method of claim 1, comprising monitoring the proliferation capacity index using microscopy.

6. The method of claim 5, wherein the microscopy comprises time-lapse video microscopy and Immunofluorescence (IF) microscopy.

7. The method of claim 1, wherein the proliferation capacity index of the test compound relative to a proliferation capacity index of Exotoxin T is indicative of a therapeutically active compound.

8. The method of claim 2, wherein the protein is (CrkI/R38K) SH2 DN or (CrkI/W170K) SH3 DN mutant form.

9. The method of claim 1, wherein the proliferation capacity index is the capacity to induce proliferation within six hours after cell rounding.

10. The method of claim 1, wherein the proliferation capacity index of apoptotic cells is assessed by counting the number of mitotic cells surrounding the transfected apoptotic cells within six hours after cell rounding.

* * * * *